(12) United States Patent
Kemppainen et al.

(10) Patent No.: US 7,014,640 B2
(45) Date of Patent: Mar. 21, 2006

(54) BONE GRAFT DELIVERY DEVICE AND METHOD OF USE

(75) Inventors: John Kemppainen, Richland, MI (US); Brian Magee, Gig Harbor, WA (US); Thomas Camino, Warsaw, IN (US); Anthony Zannis, Fort Wayne, IN (US)

(73) Assignee: DePuy Products, Inc., Warsaw, IN (US)

( * ) Notice: Subject to any disclaimer, the term of this patent is extended or adjusted under 35 U.S.C. 154(b) by 153 days.

(21) Appl. No.: 10/402,595

(22) Filed: Mar. 28, 2003

(65) Prior Publication Data

US 2004/0193170 A1    Sep. 30, 2004

(51) Int. Cl.
*A61F 5/00* (2006.01)
(52) U.S. Cl. .......................................... 606/86
(58) Field of Classification Search ................. 606/86, 606/92, 93, 94, 99; 222/413
See application file for complete search history.

(56) References Cited

U.S. PATENT DOCUMENTS

| | | | | |
|---|---|---|---|---|
| 1,077,810 A | * | 11/1913 | Craggs | 222/413 |
| 3,913,343 A | * | 10/1975 | Rowland et al. | 62/137 |
| 4,525,073 A | * | 6/1985 | Spinner | 366/323 |
| 4,538,920 A | * | 9/1985 | Drake | 366/181.5 |
| 4,582,097 A | * | 4/1986 | Izzi et al. | 141/1 |
| 4,589,576 A | * | 5/1986 | Knight et al. | 222/357 |
| 5,071,040 A | * | 12/1991 | Laptewicz, Jr. | 222/235 |
| 5,514,135 A | | 5/1996 | Earle | |
| 5,603,435 A | * | 2/1997 | Fenwick | 222/240 |
| 5,697,932 A | | 12/1997 | Smith et al. | |
| 5,925,051 A | | 7/1999 | Mikhail | |
| 6,019,765 A | | 2/2000 | Thornhill et al. | |
| 6,045,555 A | | 4/2000 | Smith et al. | |
| 6,062,438 A | * | 5/2000 | Ellis et al. | 222/349 |
| 6,550,957 B1 | * | 4/2003 | Mizutani et al. | 366/189 |
| 2002/0010472 A1 | | 1/2002 | Kuslich et al. | |
| 2002/0013553 A1 | * | 1/2002 | Pajunk et al. | 604/187 |
| 2002/0112981 A1 | | 8/2002 | Cooper et al. | |

OTHER PUBLICATIONS

"Osteosel® Injectors Precision Placement Instruments," Wright Medical Technology, Inc., © 2001, 2 pages.

* cited by examiner

*Primary Examiner*—Eduardo C. Robert
(74) *Attorney, Agent, or Firm*—Maginot, Moore & Beck (57) ABSTRACT

A dispensing device for granule bone graft of varying and/or irregular shape is characterized by a body defining a handle/hopper portion, a dispensing portion, and a feed system. The subject device permits reloading or refilling of bone graft at the time of use of the device. The bone graft dispensing device also accepts vials of bone graft. The vials are loaded onto and releasably retained by the dispensing device. In both forms, the feed system allows a controlled and/or variable rate of flow of bone graft during dispensing. The subject device may be made disposable as well as re-usable. The subject device is also modular in design allowing easy assembly/disassembly. The is subject bone graft dispenser is particularly suited for the dispensing of dry, particulate and/or granule bone graft. Particularly, the bone graft dispensing device is especially suited for the dispensing of particulate or granule bone graft having particulates or granules of various and/or irregular size, shape and combinations thereof.

20 Claims, 7 Drawing Sheets

BONE GRAFT DELIVERY DEVICE AND METHOD OF USE

BACKGROUND

1. Field of the Invention

The present invention relates to devices for the application of a bone graft material to a bone and, more particularly, to a device for the delivery of particulate bone graft material to a bone.

2. Background Information

In many orthopedic procedures, it may become necessary at some point to provide bone graft material to a bone in order to augment the natural bone. Bone graft material may include either autogenous bone, allograft, xenograft, or synthetic bone graft substitute. In many orthopedic surgical procedures, particularly joint replacement surgery, certain implantable components must be affixed to bone. The bone quality of a patient, in an area at which a prosthetic component is to be implanted, must be sufficient to enable the effective anchoring of the prosthetic component to the bone. In such situations, bone graft is thus used to provide bone augmentation, particularly for prosthetic implantation. In the case of bone defects, such defects are often also treated with a synthetic or natural bone graft. Bone graft is also used in cavities caused by tumor removal or volume lost by large fracture sites.

The use of bone graft is typically required in the case of implant revision surgery. In implant revision surgery, a previously implanted prosthesis is removed and replaced with a new prosthesis. Bone graft is used since the cavity formed by removal of the previously implanted prosthesis and any old bone cement, particulate debris, membrane, beads and other remnants associated with cemented or cementless prosthesis removal results in a cavity significantly larger than is desired for implantation of a new prosthesis.

Bone graft may be in wet or slurry form, or a dry or particulate/granule form. With respect to synthetic bone graft, the market is currently quite competitive. Many companies now provide various forms of synthetic bone graft.

The method of delivery of bone graft to a particular location depends on the form of the bone graft being utilized. In the case of wet and/or slurry type bone graft, various "caulk-type" applicators have been devised. One such device is provided in U.S. Pat. No. 5,925,051 issued to Mikhail on Jul. 20, 1999 (the "Mikhail device"). The Mikhail device provides a caulking gun type dispenser for introducing and compacting bone graft in an enlarged bone (e.g. femoral) cavity. The dispenser includes a barrel pre-loaded with bone graft and a cannulated ejector/compactor positionable over a multi-section guide wire for both ejecting bone graft from the barrel and compacting the bone graft material while being guided on the guide wire. The Mikhail device, however, is designed for use with the wet or slurry forms of bone graft.

U.S. Pat. No. 6,019,765 issued to Thornhill et al. on Feb. 1, 2000 (the "Thornhill device") teaches a bone allograft applicator device. The bone allograft applicator is used to apply a bone graft slurry to an artificial joint without having to remove a previously implanted prosthesis component. The applicator device includes a hollow tube with an actuation mechanism for discharging the bone slurry from the device via a nozzle coupled to a distal end of the tube. The bone allograft device can include various components for loading the device with the slurry and/or a plurality of nozzles each having a geometry suited for a particular application. Like the Mikhail device, the Thornhill device is designed for use with bone slurry.

Further, in U.S. Pat. No. 5,697,932 issued to Smith et al. on Dec. 16, 1997 (the "Smith device") a bone graft delivery system and method is shown. A hollow tube of pre-loaded bone graft and a plunger are used to facilitate delivery of the bone graft to a bone graft receiving area. Positioning structure is provided on the plunger to maintain the plunger in a desirable position with respect to the hollow tube. Adjunct positioning means may also be provided to ensure that the plunger remains in the desirable position during the packing of bone graft into the bone graft receiving area. Like the previous devices, the Smith device is clearly designed for wet or slurry type bone graft.

Such prior art bone graft applicators must come pre-loaded with bone graft or require constant loading, if possible, in order to constantly have a supply of bone graft available. Moreover, these devices cannot handle particulate bone graft of varying or irregular particulate size. These problems can be a huge inconvenience.

It should be appreciated in view of the above that it is desired to have a device that accurately delivers or dispenses bone graft in a timely and controlled manner to a particular bone graft receiving location. It would further be desirable to have a bone graft dispensing device that is refillable during use.

It should be further appreciated that it is desired to have a bone graft delivery device that dispenses dry and/or particulate bone graft in a controlled-flow manner. Moreover, it is desired to have a bone graft dispensing device that controllably dispenses bone graft composed of particulate of various dimensions and/or, particulate of an irregular size and/or shape.

What is therefore needed in view of the above is a bone graft dispensing device that incorporates one or more of the above-appreciated desires. What is particularly needed in view of the above is a dispensing device for dry bone graft is that allows controlled delivery of bone graft. What is more particularly needed in view of the above is a controlled application dispensing device for particulate bone graft wherein the particulate may be of irregular size and/or shape.

SUMMARY

The subject invention is a device and/or method of use thereof for dispensing bone graft material. In one form, the bone graft dispensing device permits reloading or refilling of bone graft at the time of use of the device. In another form, the bone graft dispensing device accepts pre-filled vials of bone graft. The vials are loaded onto and releasably retained by the dispensing device. In both forms, the dispensing device has a dispensing system that allows a controlled and/or variable flow rate of bone graft.

According to an aspect of the subject invention, the bone graft dispensing device may be made disposable as well as re-usable. The bone graft dispensing device is also modular in design which allows the dispensing device to be easily assembled, disassembled, cleaned and/or the like.

The bone graft dispensing device is particularly suited for the dispensing of dry bone graft. Particularly, the bone graft dispensing device is especially suited for the dispensing of particulate or granule bone graft material. More particularly, the bone graft dispensing device is especially suited for the dispensing of bone graft having particulates or granules of various and/or irregular sizes and shapes.

In one form, there is provided a device for the dispensing of dry bone graft. The device includes a body, a first chamber formed in the body and adapted to hold dry bone graft, an inlet in communication with the first chamber and adapted to receive dry bone graft during use of the device, a second chamber formed in the body and adapted to temporarily hold dry bone graft, an outlet in communication with the second chamber, and a bone graft feed system carried by the body and providing selectively controlled communication between the first chamber and the second chamber. The dry bone graft is provided to the second chamber from the first chamber by the bone graft feed system and dispensable from the second chamber through the outlet via gravity.

In another form, there is provided a device for the dispensing of dry bone graft. The device includes a first body having a bone graft retention chamber therein, a retention chamber outlet in communication with the bone graft retention chamber, and a retention chamber inlet in communication with the bone graft retention chamber; a second body having a dispensing chamber therein, a dispensing chamber outlet in communication with the dispensing chamber, and a dispensing chamber inlet in communication with the dispensing chamber and configured to slidably receive the retention chamber outlet; and a biasing member disposed between the first body and the second body. The biasing member allows controlled, selective communication between the retention chamber outlet and the dispensing chamber to provide a first state of operation, a second state of operation, and a third state of operation. The first state of operation prevents communication between the retention chamber outlet and the dispensing chamber preventing flow of bone graft from the retention chamber outlet to the dispensing chamber, the second state of operation allowing fully open communication between the retention chamber outlet and the dispensing chamber allowing fully open flow of bone graft from the retention chamber to the dispensing chamber, and a third state of operation allowing a variably intermediate flow of bone graft from the retention chamber outlet to the dispensing chamber, the variably intermediate flow of bone graft having a variable rate of flow being between the first state and the second state.

In yet another form, there is provided a device for the dispensing of dry bone graft. The device includes a body, a bone graft retention chamber formed in the body, an outlet in communication with the bone graft retention chamber, and a feed system carried by the body and configured to controllably advance bone graft in the bone graft retention chamber to the outlet, wherein bone graft advanced into the outlet is dispensed from the device via gravity.

BRIEF DESCRIPTION OF THE DRAWINGS

In the drawings.

Corresponding reference characters indicate corresponding parts throughout the several views. Like reference characters tend to indicate like parts throughout the several views.

DESCRIPTION OF THE PREFERRED EMBODIMENT(S)

While the invention is susceptible to various modifications and alternative forms, specific embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention.

Figure 1:
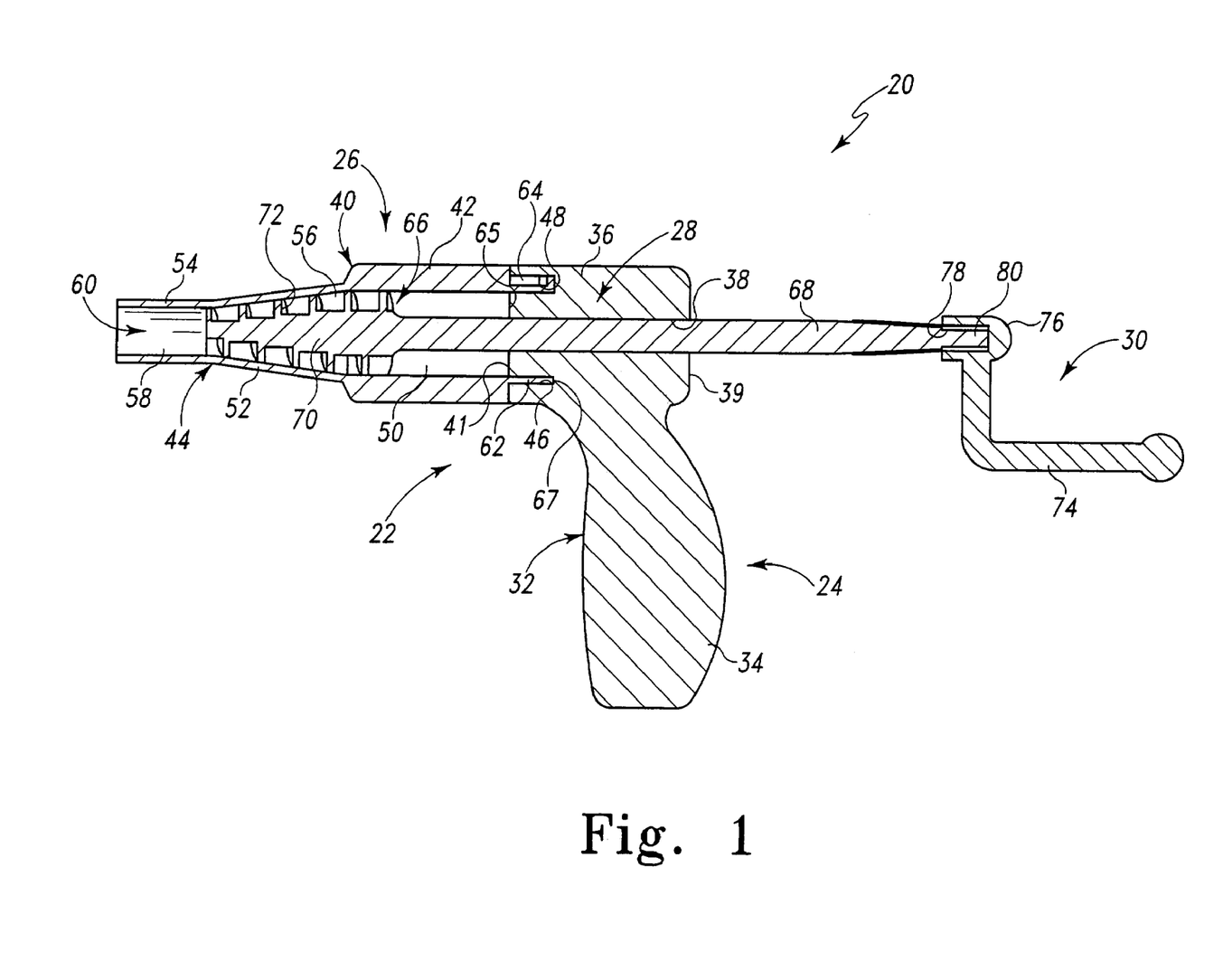
FIG. 1 is a sectional view of an exemplary bone graft delivery/application device in accordance with the principles of the subject invention.

Referring now to FIG. 1 there is shown one embodiment of a dispensing, delivery or application device (dispenser or dispensing device) for bone graft material (bone graft) generally designated 20. The bone graft dispensing device 20 is characterized by a body 22. The body 22 has a user retention portion 24, a dispenser portion 26, and a feed system 28.

The user retention portion 24 is operative to allow a user to grasp or hold the device 20. The user retention portion 24 is defined by a body 32 that is preferably, but not necessarily, manufactured from a suitable plastic. The user retention portion 24 may be manufactured from materials other than a suitable plastic as necessary, such as a suitable metal. Such materials are preferably selected with regard to the type of bone graft that will be utilized with the bone graft dispensing device 20. The body 32 defines a handle or handle portion 34 and head or head portion 36. Preferably, the handle portion 34 and the head portion 36 are formed integral with each other, but may be two or more pieces. The handle portion 34 is shaped in a manner that typically conforms to the shape of a user's hand when grasping the portion 34. This configuration is best seen in FIG. 2.

Figure 2:
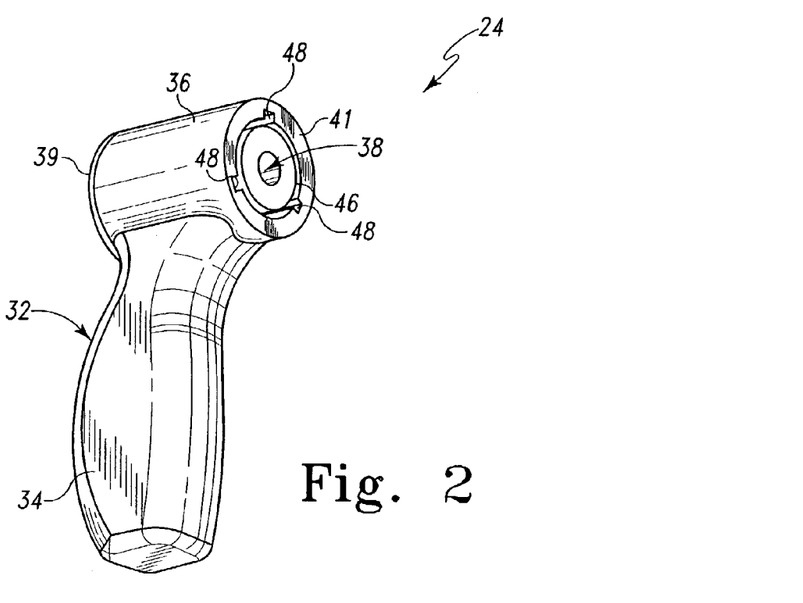
FIG. 2 is an enlarged perspective view of the handle portion of the bone graft delivery/application device of FIG. 1.

Referring additionally to FIG. 2, an enlarged depiction of the user retention portion 24 is shown. The head 36 thereof includes a bore 38 that extends from one end 39 of the head 36 to another end 41 of the head 36 opposite the end 39. It should be appreciated that while the head 36 is shown as generally cylindrical, the head 36 may take other shapes. The bore 38 is preferably cylindrical in shape and situated along a longitudinal axis of the head 36. Of course, it should be appreciated that the bore and bore placement may be different than what is shown.

The head 36 also includes a reception area 46 that is configured/operative to receive a portion of the dispenser portion 26 in order to attach the dispenser portion 26 onto the head 36. In this embodiment, the reception area 46 is formed as a slot extending into the head 36 from the end 41. Moreover, the slot 46 is substantially annular in shape and radially outside of the bore 38. The slot 46 includes at least one and preferably a multiplicity of channels, troughs, grooves or the like 48 that radially outwardly extend from the slot 46. The slot 46 and channels 48 are both of a sufficient depth as discussed below.

Figure 3:
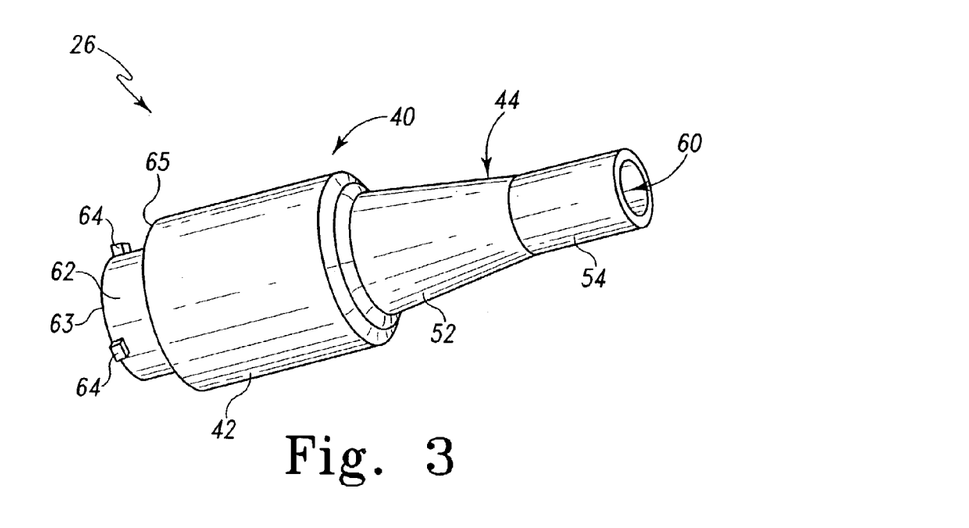
FIG. 3 is an enlarged perspective view of the dispenser portion of the bone graft delivery/application device of FIG. 1.

The dispenser portion 26 is defined by a body 40 that is preferably, but not necessarily, manufactured from a suitable plastic. The dispenser portion 26 may be manufactured from materials other than a suitable plastic as necessary, such as a suitable metal. Such materials are preferably selected with regard to the type of bone graft that will be utilized with the bone graft dispensing device 20. The body 40 has a reservoir or reservoir portion 42 and a nozzle or funnel portion 44. The nozzle 44 and the reservoir 42 are preferably, but not necessarily, formed as a single piece. Alternatively, the nozzle 44 and reservoir 42 are formed separately and joined. In this event, the nozzle may be available in various sizes (openings) to provide variable rates of flow of the bone graft and/or application amounts of bone graft.

The reservoir 42 defines an interior cavity, chamber or the like 50. In this embodiment, the reservoir 42 is cylindrical and thus so is the cavity 50. It should be appreciated that the reservoir 42 and/or the cavity 50 may have other configurations. The nozzle 44 includes a reduction portion 52 that reduces in diameter from is junction with the reservoir 42. The reduction portion 52 may be in the form of a taper, cone, or other angled surface. The reduction portion 52 also defines a reduction reservoir (a reduced diameter portion) or first feed area 56. The first feed area 56 is in communication with the reservoir 50. The nozzle 44 further includes a tip portion 54 that defines a second feed area 58 and an opening 60. The second feed area 58 is in communication with the first feed area 56. The opening 60 is in communication with the second feed area 58. The cavity 50 is sized and/or configured to receive and retain bone graft as well as a portion of the feed system 28. The amount of bone graft that the cavity 50 may hold is known, but may vary depending on the size of the reservoir 42.

Markings (not shown) may be provided on the reservoir 42 that may be used to determine the volume of bone graft in the chamber 50.

The size of the opening 60 and/or the second feed area 58 may be variable dependent upon the particulate size of the bone graft. A finer particulate size supports a smaller opening 60, while a larger particulate size supports a larger opening 60, each opening of which is determined as a function of the particulate size.

As best seen in FIG. 2, the dispensing portion 26 also includes a wall 62 that serves as a connection wall. In this embodiment, the wall 62 is annular and of a smaller diameter than the reservoir 42. The wall 62 is sized and shaped to be received in the slot 46 of the head 36 of the handle portion 24. The wall has a depth in the axial direction that is receivable in the depth of the slot 46. Preferably, but not necessarily, the depth of the wall 62 and the slot 46 coincide such that the end 63 of the wall 62 bottoms out against or reaches the end 67 of the slot 46.

The wall 62 includes one locking portion that cooperates with a second locking portion of the head 36. The two locking portions allow the reception and releasable or non-releasable (depending on the desired design) joining of the dispenser portion 26 with the handle portion 24 and, more particularly, the joining of the reservoir 42 with the head 36 (the meeting of surfaces 65 and 41). In the embodiment shown in FIGS. 1–3, the device 20 includes a first locking portion defined by a plurality of tabs 64 that each extend radially from and axially along the outside surface of the wall 62. As shown, each tab 64 begins at the end 63. The configuration of each tab 64 is formed to conform to the shape of the channels 48 in the slot 46 in the surface 41 of the head 36, forming the second locking portion. In this embodiment, the three tabs 64 correspond to the three channels 48 of the head 36. The tabs 64 are thus received in the channels 48 as the annular wall 62 is received in the slot 46. The dispenser portion 26 may or may not twist or rotate relative to the head 36 in order to temporarily or permanently lock the dispenser portion 26 onto the head 36 as necessary (e.g. utilizing the tabs 64 to interact with reversible and non-reversible locking mechanisms in the channel(s) 48 and/or the slot 46). The slot 26 and/or channels 48 would be modified accordingly to accept and provide the aforementioned feature(s)/functionality.

The dispenser portion 26 is thus assembled onto the handle portion 24. This may be accomplished at a place of manufacture or assembly such as a preassemble version, or may be accomplished more proximate the time of use such as when needed during a particular operation.

It can be appreciated that it may be desirable to control the relative orientation of the dispenser portion 26 with the head 36 and/or the handle portion 24, during assembly of the dispenser portion 26 with the head 36. To this end, each tab 64 and thus its corresponding channel 48 may be formed in a shape different from one another. In this manner, the dispensing portion 26 would be keyed to the head 36. Such keying thus allows the angular orientation of the dispenser portion 26 to be controlled relative to the head 36. Alternatively, tabs and channels may be formed in only two or more (a fixed number) shapes and used to provide mating of the dispenser portion 26 with the head 36.

The bone graft dispensing device 20 also includes the feed system 28. The feed system 28 moves the bone graft from the cavity 50 of the chamber and/or the cavity 56 of the nozzle 44 in order to make the bone graft available for dispensing. Typically, motive power for the feed system 28 is provided manually. Other, non manual means for providing motive power may also be used and are contemplated. In this manner, the feed system 28 provides for a controlled delivery and/or application of the bone graft to an appropriate location. The feed system 28 includes an auger portion 66 and an auger shaft 68. A crank 30, that may or may not be considered part of the feed system 28, is shown. The crank is preferably releasably attachable to the shaft 68, but may be permanently attachable if desired.

The crank 30 is preferably formed of the same material as the majority of or all of the other components of the subject delivery device 20. In the embodiment shown, the crank 30 has an angled portion 74 in the shape of perpendicular legs attached at ends thereof. One angled portion has an end cap 76 that defines an end cap cavity 78. The cavity 78 is configured, such as by a slight taper, to receive an end 80 of the auger shaft 68. The end 80 of the auger shaft 68 may likewise be slightly tapered. It can be appreciated that rotation of the crank 30 provides rotation of the auger shaft 68. Rotation of the auger shaft 68 provides rotation of the auger portion 66.

The auger portion 66 may be considered as having a body or body portion 70 extending from the shaft. Particularly and preferably, but not necessarily, the body 70 is coaxial with the shaft 68. In the embodiment shown, the body 70 is tapered or otherwise reduced in diameter along its length beginning at the end of the shaft 68. The body 70 includes an auger vane, fin, screw or the like 72 radially outwardly extending from the body 70 relative to a perpendicular taken along a longitudinal axis of the body 70. The auger vane 72 is configured to spiral along the outside surface of the body 70. The auger vane 72 is preferably formed integral with the body 70 but may be formed separately from the body 70 and thereafter attached to the body 70. Additionally, the auger vane 72 may be formed as two or more vanes rather than one continuous vane. When rotated, the auger vane 72 pushes, advances or feeds material (e.g. dry particulate bone graft) in the reservoir 50 through the first feed area 56 and into the second feed area 58 where gravity will provide the material from the second feed area 58 to the opening 60 thereby effecting delivery, dispensing and/or application of the material from the reservoir 50.

The auger vanes are preferably, but not necessarily, radially outwardly sized such that the outside surface thereof contacts the inner surface of the wall 52. This aids in moving as much of the bone graft as practical from the cavity 50 for application. This also aids in providing smooth rotation of the auger 66. The auger 66 is housed within the cavity 56 such that effectively no wobble can occur.

Rotation of the auger 66 is effected through rotation of the shaft 68 through rotation of the handle or crank 30. The shaft 68 is rotatably received in the bore 38 of the head 36, i.e. the shaft 68 extends through the bore 38 in the head 36 from one side 41 through another side 39. The shaft 68 is of a length to accommodate the handle 30 and provide easy use.

Figures 4, 5:
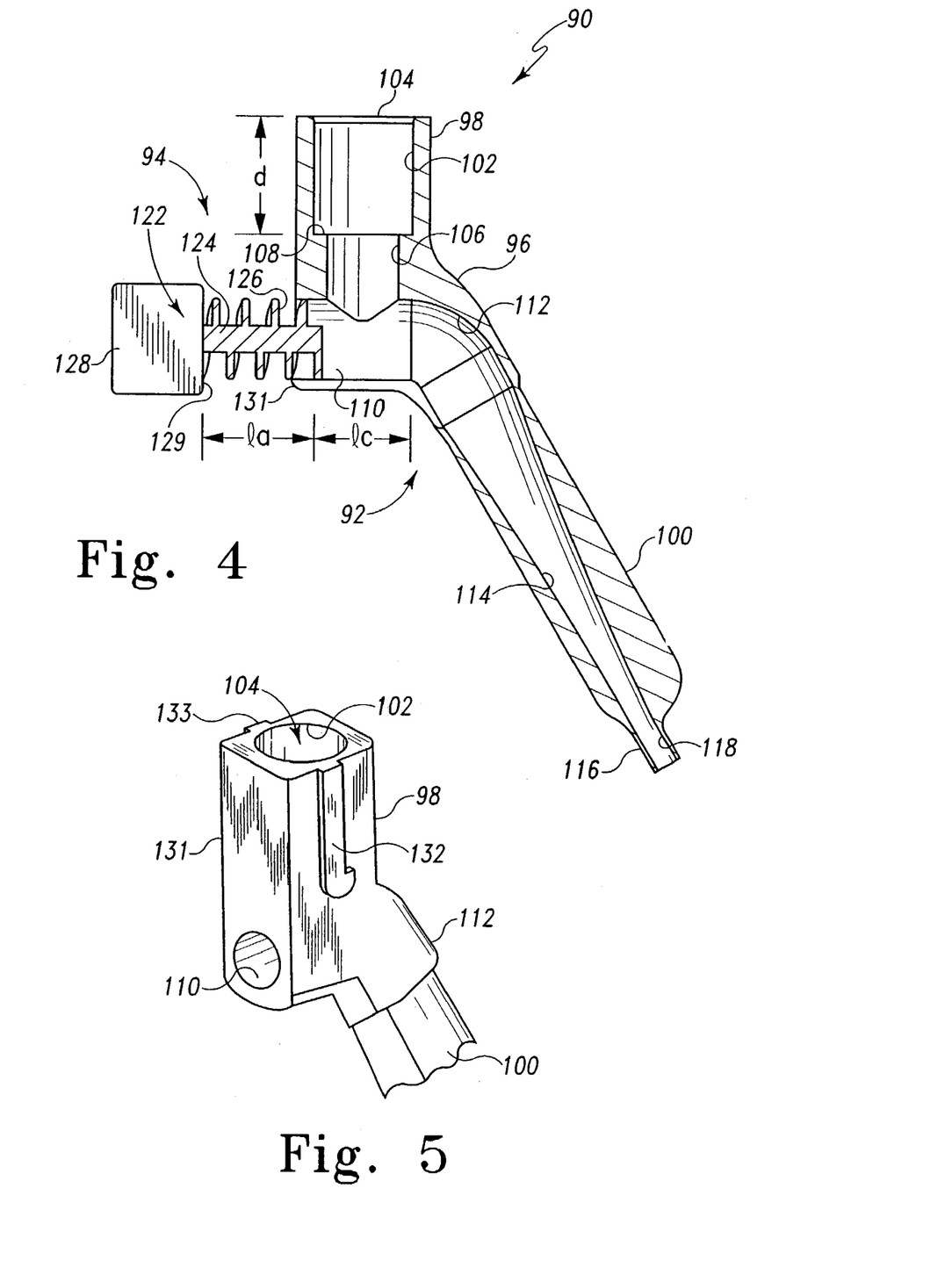
FIG. 4 is an exemplary embodiment of an alternative dispenser portion for the bone graft delivery/application device of FIG. 1.
FIG. 5 is a sectional view of an alternative embodiment of exemplary components for a bone graft dispensing device.

Referring now to FIGS. 4 and 5, there is depicted selected components of an alternative embodiment of a bone graft dispensing device 90. The selectively depicted components 90 may be used for like components of the device 20, particularly as noted. The bone graft dispensing device 20 utilized a closed container with a set of amount of bone graft therein. While not limiting, this design facilitates the use of the device as one-time or disposable unit. The bone graft dispensing device 90, however, lends itself to the continued use thereof for at least a period of time through acceptance of vials or the like containing bone graft. Use of labeled vials of bone graft material provides the ability to recognize, use, and/or control the amount and type of bone graft to be dispensed. This also allows for the ability to switch types of bone graft.

The components 90 include a dispenser portion 92 and a feed system 94. The dispenser portion 92 has a body 96 that is preferably made from the same materials as set forth above. The body 96 is configured into a hopper 98 and a nozzle, spout, funnel or the like 100. The hopper 98 has a bore 102 that defines an opening 104. The bore 102 has a depth d and a given diameter that is preferably of a dimension to receive a vial of bone graft, the vial being a particular size such as per a standard or the like. As depicted in FIG. 4, the opening 104 is slightly radially outwardly tapered from the bore 102. This conical section provides a guide for a vial of bone graft. The bore 102 defines a hopper area or first feed area.

A second bore 106 is provided at the base of the bore 102 and is thus in communication with the bore 102. The second bore 106 is preferably, but not necessarily, coaxial with the bore 102, but has a diameter that is less than the diameter of the bore 102, at least at the bottom thereof. This difference in dimensions creates a ledge or shelf 108 between the bore 102 and the bore 106. The ledge 108 provides a stop for the vial of bone graft. Moreover, the second bore 106 may be considered a second feed area.

The second feed area 106 is in communication with an auger area 110. The auger area 110 is dimensioned to receive an auger 122 or other appropriate feed system. The auger area 110 is next in communication with an elbow bore 112, while the elbow bore 112 is in communication with a funnel bore 114 of the nozzle 100. The funnel bore 114 terminates in a tip bore 118 of the tip 116. The tip bore 118 provides communication with the exterior of the device 90 in order to apply the bone graft from the hopper 98 to the desired and/or appropriate location. Control of the amount of bone graft that is provided to the tip bore 118 is accomplished in this embodiment by the feed system 94 and, more particularly, by the auger 122.

The auger 122 is characterized by a body 124 in the form of a shaft. The shaft includes a radial vane 126 on an outside surface of the body 124. The radial vane 126 is preferably, but not necessarily, a continuous vane in the form of a screw blade or the like. The vane is preferably of a constant radius along its axial or longitudinal length. The axial length la of the auger 122 is approximately the length lc of the auger area 110. Additionally, the radial length of the vane 126 is approximately equal to (i.e. slightly less than) the diameter of the inside surface of the auger area 110. The auger 122 extends from a body 128 of the device 90. The body 128 has a surface 129 that preferably abuts a surface 131 of the body 96 adjacent the auger area 110 opening when the dispenser portion 92 is attached to the feed portion 94. Rotation of the auger 122 may be accomplished in the same manner as the device 20 of FIGS. 1–3.

In operation, bone graft is loaded into the hopper 98. The dispenser portion 92 is assembled onto the feed portion 94 such that the auger 122 is situated within the auger or feed area 110 of the body 96. The bone graft falls via gravity into the second feed area 106 and into the auger area 110. Rotation of the auger 122 in the clockwise direction causes the vanes 126 to rotate thereby advancing the bone graft in the auger area 110 to be advanced toward the neck 112. Gravity and/or continued advancing of the bone graft by the auger 122 pushes the bone graft out of the tip 116. Of course, it should be appreciated that angling the vanes 126 in the opposite direction would require a counterclockwise rotation in order to advance the bone graft in the auger area 110 toward the nozzle 100).

As indicated above, the bone graft dispensing device of FIG. 4 is adapted, configured and/or operative to receive bone graft from containers such as vials that are pre-loaded with a bone graft of a particular composition and/or mean particulate size rather than using the hopper 98 in an open-fill manner. To this end, the dispensing portion 92 includes a manner of assuring that the vial of bone graft is appropriately retained on the hopper and preferably as well that the vial is also fixed thereto at least temporarily. In FIG. 5, an exemplary embodiment of such a system is depicted. The embodiment of FIG. 5 may be considered as part of the embodiment of FIG. 4, or may be a separate embodiment.

FIG. 5 provides a perspective view of the hopper portion 98 of the dispensing portion 92 of the device 90. The hopper 98 includes a vial receiving structure that is configured, adapted and/or operative to receive and retain, and preferably release, a vial of bone graft material. The vial receiving structure, in this embodiment, includes a first rib, protrusion, configured convexity, or the like 132 on an outside surface of the hopper 98 and a second rib, protrusion, configured convexity, or the like 133 on the outside surface of the hopper 98 opposite the first rib 132. Each rib 132, 133 extends a length of the outside surface of the hopper 98, generally in a coaxial direction relative to the bore 102. The ribs 132, 133 are configured to receive a complementarily-configured vial (not shown) or a complementarily-configured vial housing (i.e. vial within a housing, not shown). The vial receiving structure may include structure to at least temporarily lock the vial in place for use. The vial receiving structure of the hopper 98 may also provide quick connect/ disconnect of bone graft containers (e.g. vials) for dispensing.

It should also be appreciated that the auger embodiments described above, exact a positive pressure on the bone graft in order to move or advance the bone graft from the bone graft chamber into the dispensing chamber. As such, the auger embodiments may support the dispensing of a putty, slurry or sludge type bone graft. Such a bone graft material would be caused to flow from the bone graft dispenser via positive pressure exerted on the putty-like bone graft material by the auger feed system.

Figure 6:
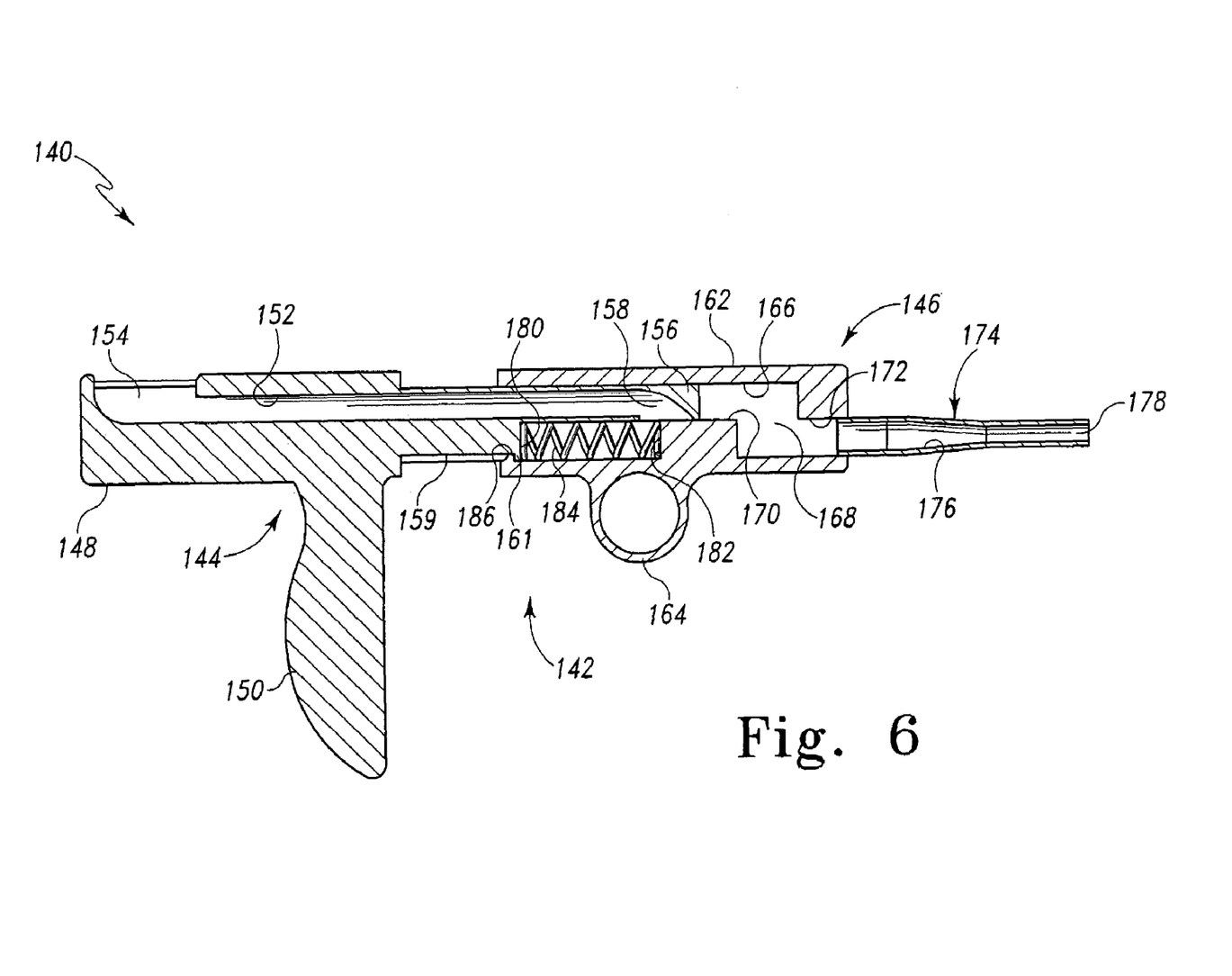
FIG. 6 is a side sectional view of another alternative embodiment of a bone graft dispensing device in accordance with the present principles.

Referring now to FIG. 6, there is depicted an alternative embodiment of a bone graft delivery/application/dispensing device generally designated 140. The bone graft delivery device 140, like the bone graft dispensing devices discussed hereinabove, is operative, configured and/or adapted to dispense, deliver, apply or the like (collectively, "dispense") bone graft, the bone graft preferably being dry bone graft material and, more particularly, dry, particulate bone graft material. The device 140 is further operative, configured and/or adapted to utilize, at least in part, gravity for assisting in the dispensing of the bone graft.

The bone graft delivery device 140 is characterized by a body 142 that may be divided into various portions or sections. As such, the body 142 includes a combination handle/hopper portion 144 and a dispensing portion 146. In an assembled state, the dispensing portion 146 is disposed on a portion of the handle/hopper portion 144. The handle/hopper portion 146 is operative, configured and/or adapted to provide a user the ability to hold the device 140 and to receive and retain bone graft material for eventual dispensing. The dispensing portion 146 is operative, configured and/or adapted to allow the user to selectively dispense bone graft. Particularly, the dispensing portion 146 cooperates with the handle/hopper portion 144 in conjunction with a return and stop mechanism discussed below.

Particularly, the handle/hopper portion 144 is characterized by a body 148 that is preferably made of the same material as the other bone graft application devices described herein. The body 148 includes a handle 150 that is integrally formed with a reservoir portion 152. The reservoir portion 152 is operative to receive and retain bone graft for eventual dispensing. In the embodiment shown, the reservoir 152 is in the form of an elongated cavity. Particularly, the cavity 152 is formed in the body 148 that includes a conduit portion 156. The cavity 152 extends through the conduit 156 and is in communication with an opening 158.

The dispenser portion 146 is characterized by a body 162 having a passage 166 therein. The passage 166 is configured to slidably receive the conduit 56 of the body 148. A hopper area 168 is provided in the body 162 that is in communication with the passage 166. The dimensions, size and/or volume of the hopper area 168 may be of a particular size (such as 10 cc). The passage 166 has a block, stop, or the like 170 therein. The block 170 provides a partition that aids in defining the hopper area 168. The body 162 further has a bore 172 that is in communication with the hopper area 168 and the outside of the body 162. A nozzle 174 is preferably, but not necessarily, situated in an end of the body 162 in the bore 172. The nozzle 174 has an interior hollow 176 that provided communication between the bore 172 and an opening 178 of the nozzle 174. The hollow 176 preferably, but not necessarily, reduces in diameter from the bore 172 of the body 162 toward the opening or tip 178. The body 162 may accept nozzles of various sizes particularly, of different lengths and/or openings. The various nozzles may be designed for a particular granular bone graft size or range of sizes or for various surgical applications.

It can be easily seen that once the bone graft is in the hopper area 168, appropriate positioning of the device 140 will allow gravity to feed the bone graft material into the nozzle and out the opening 178. Bone graft is provided to the hopper area 168 via a feed system including, in this embodiment, components and/or features of both the dispenser portion 146 and the handle/hopper portion 144. Particularly, the conduit 156 interacts with the stop 170 and the passage 166 to provide communication between the opening 158 of the conduit 156 and the hopper area 168. Bone graft that has been loaded into the cavity 152 (via the cavity opening 154) is controllably provided to the hopper area 168 for eventual dispensing or application to a particular location via the nozzle 174.

The handle/hopper portion 144 is operatively coupled to the dispensing portion 146 to provide controlled and/or selective dispensing or application of bone graft. With respect to this aspect, the body 162 of the dispensing portion 146 includes a stop 186 proximate the opening of the passage 166. The stop 186 may take many forms, but is here shown as a protrusion extending into the passage 166. The body 148 of the handle/hopper portion 144 includes a groove, channel or the like 159 defining a stop 161. The groove 159 is configured to slidably receive the stop 186. The stop 161 is configured to interact with the stop 186 to prevent the two bodies 148 and 162 from becoming disassembled. Particularly, the stops 161 and 186 restrict or stop axial movement of the body/conduit 148/156 within the body/passage 162/166 when the device 140 is in a loading or non-dispensing mode or state. The device 140 is biased so as to be in the loading or non-dispensing mode. To this end, a biasing or resilient member 184, here depicted as a spring, is provided to interact on and between the body 148 and the body 162.

Particularly, the spring 184 is seated at one end thereof against a surface 180 of the body 148, and seated at another end thereof against a surface 182 defined by the block 170. The spring 184 is retained in the area bounded by the surfaces 180 and 182, and the conduit 156. While the conduit 156 and the passage 166 may take on many configurations, but typically only complementary configurations, the conduit 156 and at least a portion of the passage 166 has a rectangular cross-section. This defines a generally rectangular spring area as well.

Figure 7:
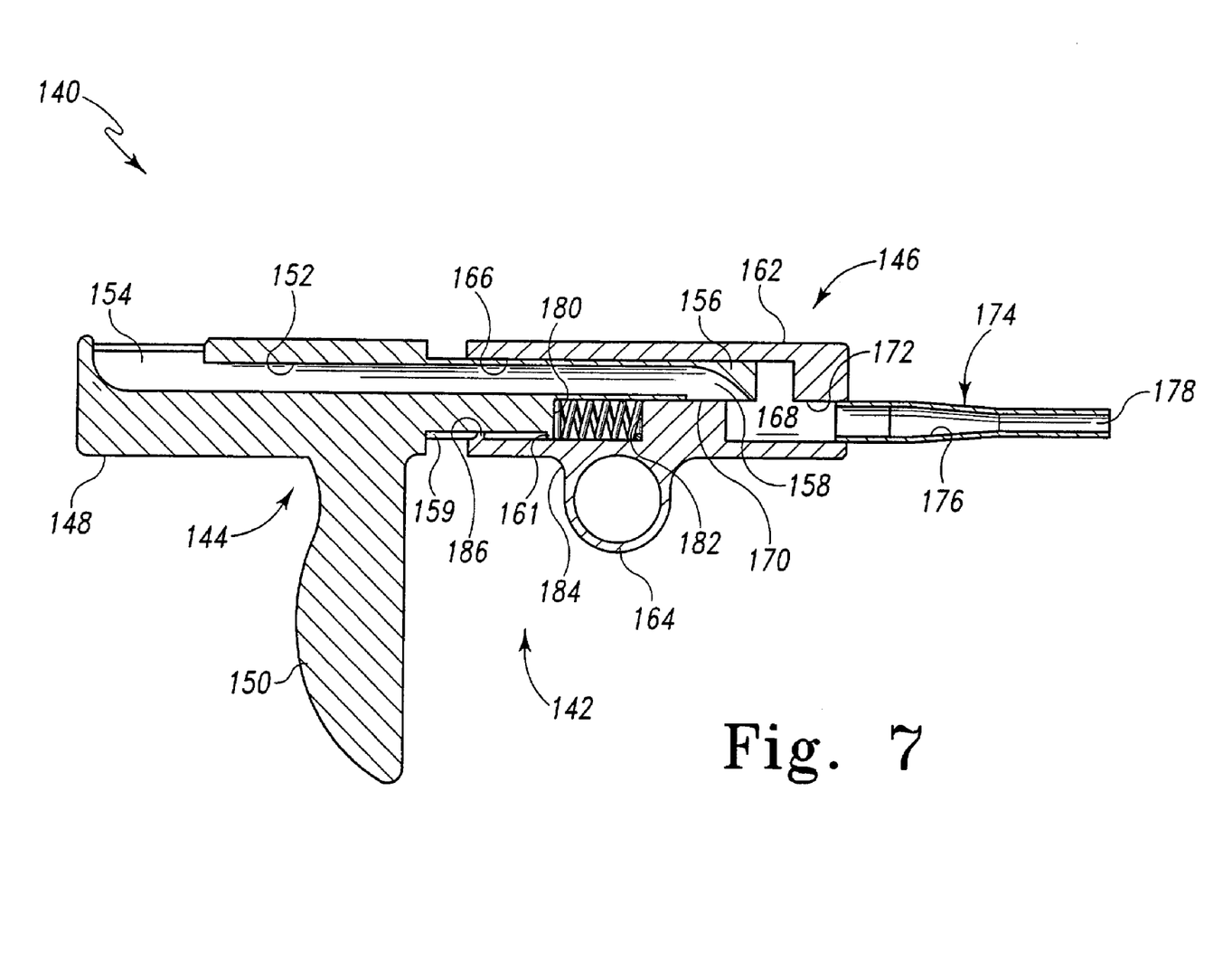
FIG. 7 is a side sectional view of the bone graft dispensing device of FIG. 6 illustrating the bone graft dispensing device in a partial dispensing position.
Figure 8:
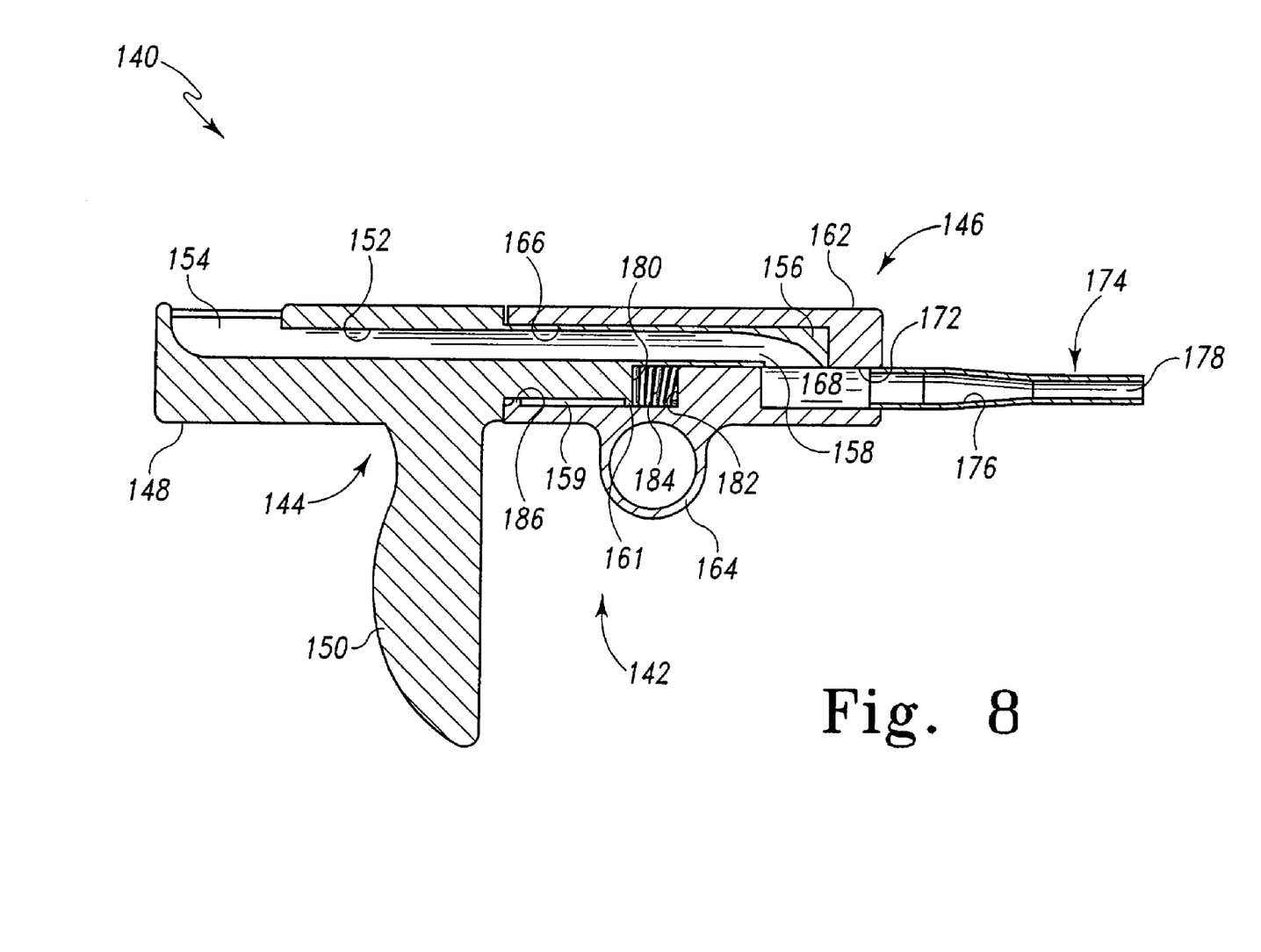
FIG. 8 is a side sectional view of the bone graft dispensing device of FIG. 6 illustrating the bone graft dispensing device in a full dispensing position.

Referring additionally to FIGS. 7 and 8, a manner of operation of the device 140 is illustrated in conjunction with the device 140 depicted in FIG. 6. As indicated above, the device 140 as illustrated in FIG. 6 is in a non-dispensing mode, state, position, or the like. In FIG. 7, the device 140 is shown in a partial dispensing mode, state, position or the like (i.e. a position between fully open or dispensing and fully closed or not dispensing). In FIG. 8, the device 140 is shown in a fully open (dispensing) mode, state, position or the like. The distance the opening 158 travels beyond the edge of the stop 170 towards the nozzle 174 defines the position, mode or state of the device 140. When the opening 158 is completely covered by the block 170 as depicted in FIG. 6, no bone graft is able to fall from the opening 158 into the hopper area 168. When only some of the opening 158 is covered by the stop 170 (or only a portion of the opening is beyond the edge of the stop 170) as depicted in FIG. 7, a selective, variable, or controlled rate of flow of bone graft is supplied to the hopper area 168. This variable rate of flow allows the amount of bone graft that is supplied to the nozzle 174 for dispensing to be controlled. The more that the opening 158 is in communication with the hopper area 168, the greater the rate of flow. The less that the opening 158 is in communication with the hopper area 168, the less the rate of flow.

Particularly, in FIG. 7, the bodies 148 and 162 have been compressed against one another to overcome the biasing of the spring 184. This is accomplished by a user grasping the handle 150, extending a finger into the trigger 164, and compressing or squeezing. At the point shown, about half the area of the opening 158 extends beyond the stop 170. The device 140 may be considered to be in a 50% flow rate mode (wherein a fully open position equates to a 100% flow rate and a fully closed position equates to a 0% flow rate). The amount of pressure required to compress the two bodies 148 and 162 together depends on the spring force of the spring 184. Such tension may be a matter of design choice.

It should be appreciated that there are multiple positions of the opening/stop 158/170 represented by the position of FIG. 7, that provide more or less bone graft to the hopper area 168 (i.e. provide greater or lesser rates of flow). When the entire opening 158 is beyond the edge of the stop 170 and thus in full communication with the hopper area 168, as depicted in FIG. 8, the dispenser 140 provides maximum flow of bone graft to the nozzle 174. The spring 184 is also in its most compressed state, as compared to the lesser compressed states for FIG. 7 and the least for FIG. 6.

Figure 9:
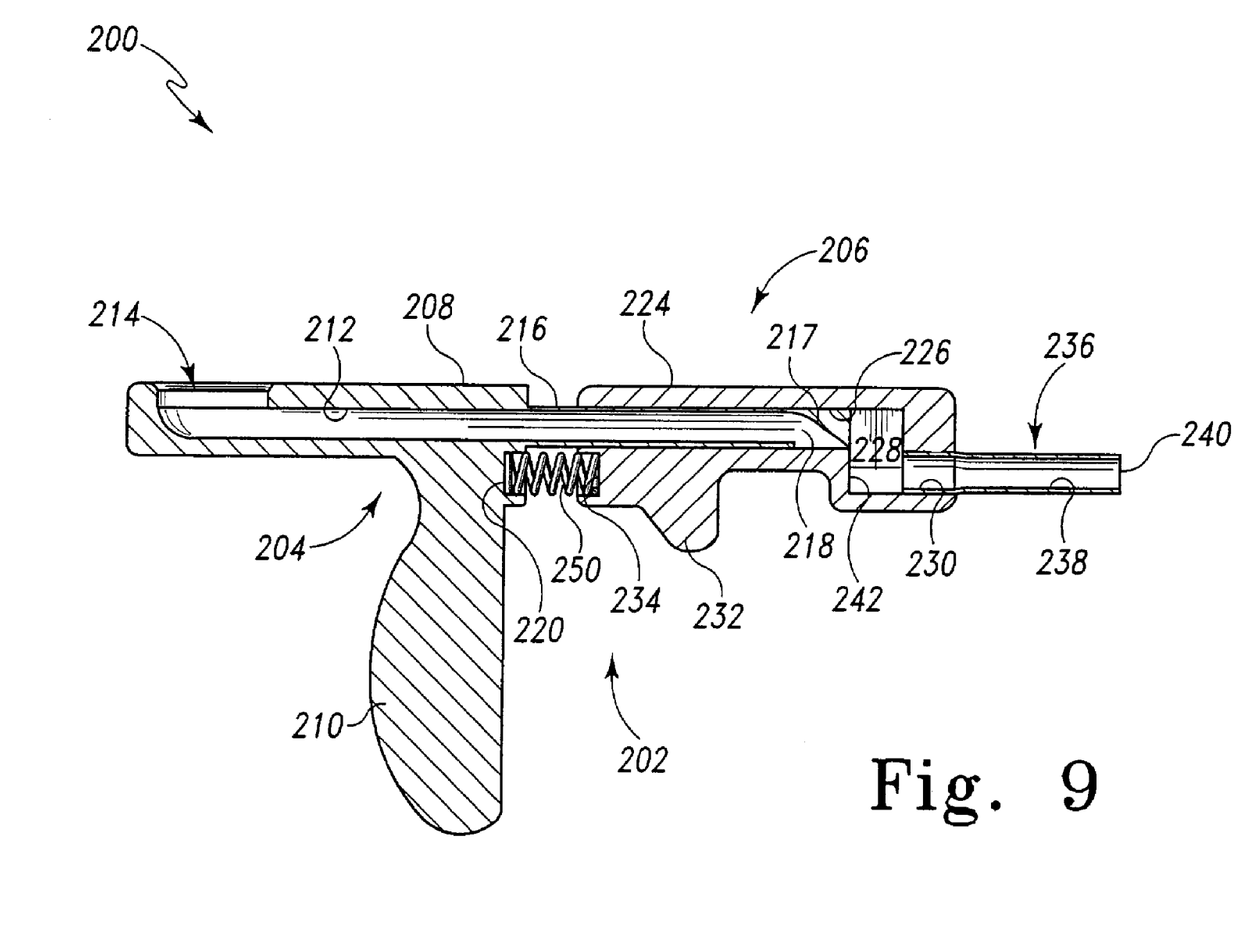
FIG. 9 is a side sectional view of yet another alternative embodiment of a bone graft dispensing device in accordance with the present principles.

Referring now to FIG. 9, there is depicted an alternative embodiment of a bone graft dispensing device generally designated 200. The device 200 functions is essentially the same manner as the previous embodiments. Thus, the bone graft delivery device 200, like the bone graft delivery/dispensing devices discussed hereinabove, is operative, configured and/or adapted to dispense, deliver, apply or the like (collectively, "dispense") bone graft, the bone graft preferably being dry bone graft and, more particularly, dry, particulate bone graft. The device 200 is further operative, configured and/or adapted to utilize, at is least in part, gravity for assisting in the dispensing of the bone graft.

The bone graft delivery device 200 is characterized by a body 202 that may be divided into various portions or sections. As such, the body 202 includes a combination handle/hopper portion 204 and a dispensing portion 206. In an assembled state, the dispensing portion 206 is disposed on a portion of the handle/hopper portion 204. The handle/hopper portion 206 is operative, configured and/or adapted to provide a user the ability to hold the device 200 and to receive and retain bone graft for eventual dispensing. The dispensing portion 206 is operative, configured and/or adapted to allow the user to selectively dispense bone graft material. Particularly, the dispensing portion 206 cooperates with the handle/hopper portion 204 in conjunction with a biasing member discussed below.

Particularly, the handle/hopper portion 204 is characterized by a body 208 that is preferably made of the same material as the other bone graft delivery/dispensing/application devices described herein. The body 208 includes a handle 210 that is integrally formed with a reservoir portion 212. The reservoir portion 212 is operative to receive and retain bone graft for eventual dispensing. In the embodiment shown, the reservoir 212 is in the form of an elongated cavity. Particularly, the cavity 212 is formed in the body 208 that includes a conduit portion 216. The cavity 212 extends through the conduit 216 and is in communication with an opening 218.

The dispenser portion 206 is characterized by a body 224 having a passage 226 therein. The passage 226 is configured to slidably receive the conduit 216 of the body 208. A hopper area 228 is provided in the body 224 that is in communication with the passage 226. The dimensions, size and/or volume of the hopper area 228 may be of a particular size (such as 12 cc). The passage 226 has an edge, ledge, or the like 242 between the passage 116 and the hopper area 228.

The edge 242 provides a partition that aids in defining the hopper area 228. The body 224 further has a bore 230 that is in communication with the hopper area 228 and the outside of the body 224. A nozzle 236 is preferably, but not necessarily, situated in an end of the body 224 in the bore 240. The nozzle 236 has an interior hollow 238 that provides communication between the bore 230 and an opening or tip 240 of the nozzle 236. The hollow 238 preferably, but not necessarily, reduces in diameter from the bore 230 of the body 224 toward the opening or tip 240. The body 224 may accept nozzles of various sizes particularly, of different lengths and/or openings. The various nozzles may be designed for a particular granular bone graft size or range of sizes or for a particular surgical application.

It can be easily seen that once the bone graft is in the hopper area 228, appropriate positioning of the device 200 will allow gravity to feed the bone graft into the nozzle and out the opening 240. Bone graft is provided to the hopper area 228 via a feed system including, in this embodiment, components and/or features of both the dispenser portion 206 and the handle/hopper portion 204. Particularly, the conduit 216 interacts with the ledge 242 and the passage 226 to provide communication between the opening 218 of the conduit 216 and the hopper area 228. Bone graft that has been loaded into the cavity 212 (via the cavity opening 214) is controllably provided to the hopper area 228 for eventual dispensing or application to a particular location via the nozzle 236.

The handle/hopper portion 204 is operatively coupled to the dispensing portion 206 to provide controlled and/or selective dispensing or application of bone graft material. With respect to this aspect, the body 224 of the dispensing portion 206 includes a biasing member reception area or concavity 234, while the body 208 of the handle/hopper portion 204 includes a biasing member reception area or concavity 220. A biasing member 250, here illustrated as a spring, is disposed in the biasing member reception areas 220 and 234. Each end of the spring 250 is fixed to the respective portion. Spring tension maintains the conduit 216 within the passage 226 such that the opening 218 is normally covered as illustrated in FIG. 9. Compression of the two portions 204 and 206 together, overcomes the spring tension and allows controlled communication between the opening 218 and the hopper area 228. The device 200 is thus capable of positions ranging from fully closed to fully open in like manner as that described in connection with the device 140.

Compression of the handle/hopper portion 204 and the dispensing portion 206 is accomplished by a user (not shown) grasping the handle 210 of the handle/hopper portion 204 with the palm of the hand, and wrapping a finger around a finger-hold 232 of the dispensing portion 206. Compression of the two portions together causes the end 217 of the conduit 216 to enter into the area 228. This provides communication between the opening 218 and the area 228. Bone graft is then deposited into the area 228 from the opening 218.

There is a plurality of advantages of the subject invention arising from the various features of the bone graft dispensing device or dispenser described herein. It will be noted that further alternative embodiments of the bone graft dispensing device of the subject invention may not include all of the features described yet still benefit from at least some of the advantages of such features. Those of ordinary skill in the art may readily devise their own implementations of a bone graft dispensing device that incorporate one or more of the features of the subject invention and fall within the sprit and scope of the subject invention.

What is claimed is:

1. A device for the dispensing of dry bone graft comprising:
   a body;
   a bone graft retention chamber formed in said body configured and sized to receive bone graft material;
   an outlet in communication with said bone raft retention chamber configured and sized to dispense bone graft material at a surgical site;
   a feed system carried by said body and configured to controllably advance bone graft in said bone graft retention chamber to said outlet, wherein bone graft advanced into said outlet is dispensed from the device via gravity; and
   dry bone graft material received in the bone graft retention chamber.

2. The device of claim 1, wherein said body includes a handle.

3. The device of claim 1, wherein said feed system comprises an auger.

4. The device of claim 3, wherein said auger is disposed in said bone graft retention chamber.

5. The device of claim 3, wherein said bone graft retention chamber is configured with inwardly sloping walls and said auger is complementarily configured.

6. A device for the dispensing of dry bone graft comprising:
   a body comprising a reservoir portion configured to include a bone graft retention chamber formed about a longitudinal axis and having a cross-sectional area perpendicular to the longitudinal axis, a nozzle portion configured to include an outlet having a cross-sectional area smaller than the cross-sectional area of the chamber and a reduction portion in fluid communication with the chamber and opening and having a cross-sectional area perpendicular to the longitudinal axis that decreases from approximately equal to the cross-sectional area of the reservoir portion adjacent a junction with the reservoir portion to approximately equal to the cross-sectional area of the opening adjacent a junction with the opening; and
   a feed system carried by said body and configured to controllably advance bone graft in said bone graft retention chamber to said outlet, wherein bone graft advanced into said outlet is dispensed from the device via gravity.

7. The device of claim 6, wherein said feed system comprises an auger assembly configured to advance dry bone graft from the bone graft retention chamber to the nozzle portion via rotation thereof.

8. The device of claim 7, wherein said auger assembly is manually actuated.

9. The device of claim 7, wherein said auger assembly comprises:
   an auger including a continuous vain and a portion of the auger including a portion of the vain is disposed in the bone graft retention chamber and a portion of the auger including a portion of the vain is disposed in the disposed is disposed in the nozzle portion;
   an auger shaft coupled at one end to said auger and extending through said body; and
   an actuator coupled to another end of said auger shaft, wherein rotation of said actuator rotates said auger.

10. The device of claim 6, wherein said outlet comprises an elongate member.

11. The device of claim 6 further comprising a handle having a longitudinal axis generally transverse to the longitudinal axis of the bone graft retention chamber.

12. The device of claim 11 wherein the handle is spaced apart from the opening.

13. The device of claim 6 wherein reservoir portion includes an orifice at an end of the bone graft retention chamber opposite the junction with the nozzle portion and wherein the body further comprises a handle portion configured to mate with the reservoir portion to block the orifice.

14. A device for the dispensing of dry bone graft, the device comprising:
   a body;
   a first chamber formed in said body and adapted to hold dry bone graft;
   dry bone graft material disposed in the first chamber;
   a second chamber formed in said body and adapted to temporarily hold dry bone graft;
   an outlet in communication with said second chamber; and
   a bone graft feed system carried by said body and providing selectively controlled communication between said first chamber and said second chamber, wherein dry bone graft provided to said second chamber from said first chamber by said bone graft feed system is dispensable from said second chamber through said outlet via gravity.

15. The device of claim 14, wherein said feed system comprises an auger assembly configured to advance dry bone graft from said first chamber to said second chamber via rotation thereof.

16. The device of claim 15, wherein said auger assembly is manually actuated.

17. The device of claim 15, wherein said auger assembly comprises:
   an auger disposed in said first chamber;
   an auger shaft coupled at one end to said auger and extending through said body; and
   an actuator coupled to another end of said auger shaft, wherein rotation of said actuator rotates said auger.

18. The device of claim 14, further comprising a nozzle in said outlet.

19. The device of claim 14, wherein said outlet comprises an elongate member.

20. The device of claim 14, wherein said body further includes a handle.

* * * * *